(12) United States Patent
Ota et al.

(10) Patent No.: US 6,514,538 B1
(45) Date of Patent: Feb. 4, 2003

(54) EXTERNAL PREPARATIONS FOR SKIN WHITENING

(75) Inventors: Naomi Ota, Yokohama (JP); Tomomi Okazaki, Yokohama (JP); Ohji Ifuku, Yokohama (JP); Hirofumi Aoki, Yokohama (JP); Kenichi Umishio, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/744,969

(22) PCT Filed: Jun. 8, 2000

(86) PCT No.: PCT/JP00/03717

§ 371 (c)(1),
(2), (4) Date: Feb. 14, 2001

(87) PCT Pub. No.: WO00/76473

PCT Pub. Date: Dec. 21, 2000

(30) Foreign Application Priority Data

Jun. 15, 1999 (JP) .............................................. 11-168107

(51) Int. Cl.$^7$ ........................ A61K 35/78; A61K 7/135; A01N 65/00

(52) U.S. Cl. .................... 424/725; 424/62; 424/773; 424/774; 424/779

(58) Field of Search ...................... 424/62, 725, 773, 424/774, 779

(56) References Cited

FOREIGN PATENT DOCUMENTS

| JP | 10-36216 | * | 2/1998 |
|----|----------|---|--------|
| JP | 10-45541 | * | 2/1998 |

OTHER PUBLICATIONS

English language abstract of JP 10-36216, Patent Abstracts of Japan, 1998.*
English language abstract of JP 10-45541, Patent Abstracts of Japan, 1998.*
English language translation of JP 10–036216, Feb. 1998.*

* cited by examiner

*Primary Examiner*—Michael G. Hartley
*Assistant Examiner*—Michael A. Willis
(74) *Attorney, Agent, or Firm*—Townsend & Banta

(57) ABSTRACT

An endermic liniment which characteristically contains an extract from a plant of the Solanaceae family (Solanaceae), genus Withania (Withania). A whitening endermic liniment with a superior whitening effect can be provided.

2 Claims, 1 Drawing Sheet

EXTERNAL PREPARATIONS FOR SKIN WHITENING

FIELD OF THE INVENTION

This invention relates in general to a whitening endermic liniment, and more particularly to a highly safe whitening endermic liniment with a substantially improved skin whitening effect.

BACKGROUND OF THE INVENTION

Pigment deposition in skin, such as with chloasma and freckles, results from the formation of melanin pigment due to hormonal abnormalities or ultraviolet light stimulation from sunlight followed by the excessive deposition of this pigment in the skin.

This melanin pigment is produced in melanin producing granules (melanosomes) in melanin cells (melanocytes) in the epidermis base layer. Melanin thus produced is then diffused to neighboring cells by means of osmosis. The biochemical reactions in the melanocytes are speculated to be those described below.

That is, the production process of melanin pigment is thought to be as follows: tyrosine, one of the essential amino acids, becomes dopaquinone through the action of the enzyme tyrosinase, and this is then changed to a red pigment, to a colorless pigment and finally to melanin, which is black, by enzymatic as well as non-enzymatic oxidation.

Therefore, in order to suppress the production of melanin, it is important to suppress the first stage of the reactions, i.e. the action of tyrosinase.

In order to prevent chloasma and freckles, there has been research on substances which would suppress melanin production. Examples of such methods include a method in which a large amount of L-ascorbic acid is administered, a method in which glutathione and such are injected, and a method in which hydroquinone, kojic acid, cysteine, etc. are blended in an endermic liniment such as ointment, cream, and lotion, and applied locally.

However, many of these have problems in terms of stability, safety, odor, etc. Also, the expected effect is weak and unsatisfactory.

Based on the aforementioned situation, the inventors conducted earnest research to obtain an endermic liniment with a superior whitening effect which is highly stable and safe, and discovered that an extract from a plant of the Solanaceae family (Solanaceae), genus Withania (Withania), has the tyrosinase activity suppression effect and the melanin production suppression effect and that an endermic liniment with a superior whitening effect can be obtained by blending this extract into an endermic liniment, thus completing the present invention.

The object of the present invention is to provide a whitening endermic liniment with a superior whitening effect which is highly stable and safe.

DISCLOSURE OF THE INVENTION

That is, the present invention provides a whitening endermic liniment which characteristically contains an extract from a plant of the Solanaceae family (Solanaceae, genus Withania (Withania).

Also, the present invention provides said whitening endermic liniment wherein said plant of the Solanaceae family (Solanaceae), genus Withania (Withania), is Musali (common name; Musali, scientific name; *Withania somnifera*).

Furthermore, the present invention provides said whitening endermic liniment wherein the blend ratio of said extract from a plant of the Solanaceae family (Solanaceae), genus Withania (Withania), is 0.0001–20.0 wt % of the total amount of the whitening endermic liniment.

Also, the present invention provides said whitening endermic liniment wherein the blend ratio of said extract from a plant of the Solanaceae family (Solanaceae), genus Withania (Withania), is 0.0001–20.0 wt % of the total amount of the whitening endermic liniment.

Furthermore, the present invention provides a skin whitening method which characteristically applies said whitening endermic liniment onto skin.

Also, the present invention provides a melanin production suppressing agent which characteristically consists of an extract from a plant of the Solanaceae family (Solanaceae), genus Withania (Withania).

Furthermore, the present invention provides said melanin production suppressing agent wherein said plant of the Solanaceae family (Solanaceae), genus Withania (Withania), is Musali (common name; Musali, scientific name; *Withania somnifera*).

Also, the present invention provides a tyrosinase activity suppressing agent which characteristically consists of an extract from a plant of the Solanaceae family (Solanaceae), genus Withania (Withania).

Furthermore, the present invention provides said tyrosinase activity suppressing agent wherein said plant of the Solanaceae family (Solanaceae), genus Withania (Withania), is Musali (common name; Musali, scientific name; *Withania somnifera*).

BRIEF DESCRIPTIONS OF THE DRAWINGS

THE BEST MODES OF THE EMBODIMENTS

Figure 1:
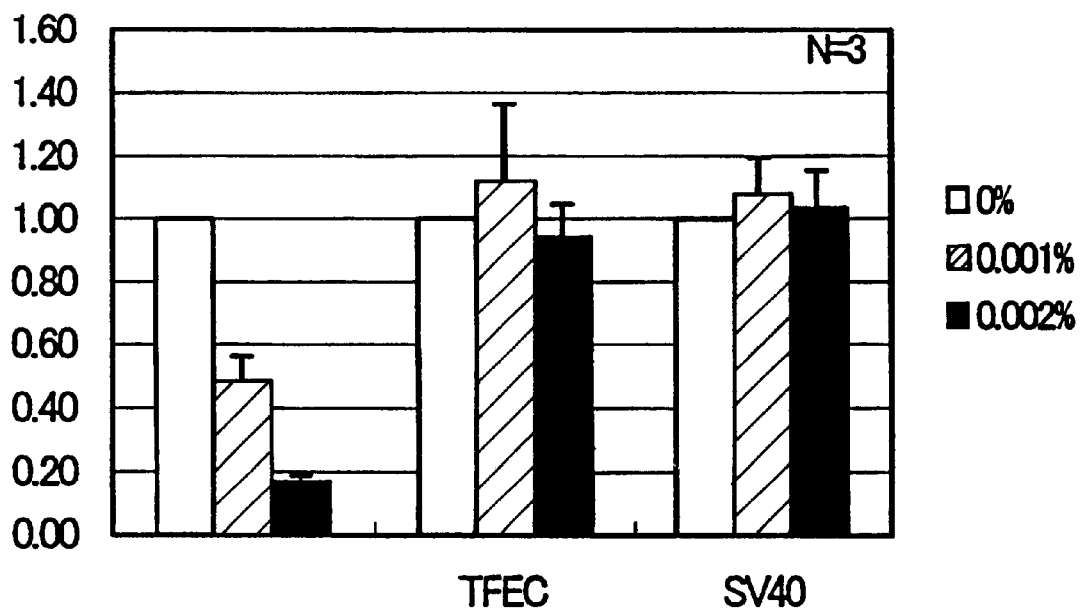
FIG. 1 is a graph showing changes in the tyrosinase promoter activity caused by the Musali extract.

The present invention is described in detail below.

For the plant of the Solanaceae family (Solanaceae), genus Withania (Withania), used in the present invention, Musali (common name; Musali, scientific name; *Withania somnifera*) is preferable. Musali (common name; Musali, scientific name; *Withania somnifera*) is a plant of the Solanaceae family, genus Withania, with distribution in Nepal, the western India, and South Africa. The melanin production suppression effect of the extract of the plant of the Solanaceae family (Solanaceae), genus Withania (Withania), was first discovered by the inventor. Its application in whitening agents and whitening endermic liniments is not known at all.

The extract used in the present invention is obtained by immersing or heated refluxing of leaves, tubers, stems, fruits, etc. or the whole aforementioned plant in an extraction solvent, followed by filtering and condensation. The extraction solvent used in the present invention can be any solvent which is normally used for extraction. Examples include alcohols such as ethanol, hydrated alcohols, and organic solvents such as acetone and ethyl acetate, and these can be used either independently or in combination.

The blend ratio of the extract of a plant of the Solanaceae family (Solanaceae), genus Withania (Withania), used in the endermic liniment of the present invention is not limited in particular. Generally, the blend ratio, in a dry form, is 0.0001–20 wt %, preferably 0.001–10 wt %, more preferably 0.01–7 wt %, of the total amount of the endermic liniment. If this blend ratio is less than 0.0001 wt % then the whitening effect of the endermic liniment tends to be poor. On the other hand, if it is more than 20 wt % no substantial increase in the effect can be expected and blending into the endermic liniment tends to be difficult.

In addition to the essential ingredient described above, the endermic liniment of the present invention can contain, as necessary, those ingredients such as are normally used in cosmetics, drugs, etc. in the form of an endermic liniment, including oil-based ingredients, humectants, ultraviolet light absorbents, antioxidants, surfactants, preservatives, perfumes, water, alcohol, and thickeners. The endermic liniment of the present invention can be prepared with a conventional method using the aforementioned ingredients.

The endermic liniment of the present invention can be in any form which is conventionally used as an endermic liniment, including a solubilized system such as lotion, an emulsified system such as emulsion and cream, as well as ointment, dispersion, and packs.

EXAMPLES

The present invention is described in detail by referring to examples below. The technical scope of the present invention is not limited to these examples. The blend ratios in examples are indicated in weight percent units.

Before explaining the examples, the testing methods and the results of the melanin suppression effect, the tyrosinase activity suppression effect and the whitening effect of the plant extract of the present invention are described. The blend ratios are indicated in weight percent units.

1. Preparation of the Musali Extract

Raw plants (roots) of Musali (common name; Musali, scientific name; *Withania somnifera*) were immersed in methanol at room temperature for a week. The extract solution was then concentrated to obtain the Musali extract. This extract was dissolved in DMSO to obtain a 1% solution, and this solution was diluted to adjust the concentration for the following tests and Examples.

2. Cell Culture

B16 melanoma culture cells from mice were used. A culture was conducted in a $CO_2$ incubator (95% air and 5% carbon oxide) at 37° C. using Eagle's EM medium containing 10% FBS and theophylline (0.09 mg/ml). After 24 hours of culturing, the sample solution was added to it such that the final concentration (in dried extract) was $10-2-10^{-5}$ wt %. The culture was continued for 3 more days, and melanine production was visually evaluated and the tyrosinase activity was measured.

3. Visual Evaluation of the Amount of Melanin

A diffusion plate was placed on top of the lid of the plate of 96 wells, and the amount of melanin in the cells was evaluated using an inverted microscope. The evaluation was compared with that of a sample with no added plant extract (control sample). The results are shown in Table 1.

For a reference, the same testing was conducted on *Nepeta japonica* Maxim. (*Lamium album* L. subfamily, perilla family) extract which was already known to suppress melanin production. These results are also shown in Table 1.

<Criteria>

◯: Whiter compared with the control (the amount of melanin is less compared with the control).

Δ: Somewhat whiter compared with the control (the amount of melanin is somewhat less compared with the control).

×: Equivalent to the control (the amount of melanin is equivalent to that of the control).

4. Tyrosinase Activity Measurement

Before the measurement the medium was removed, followed by washing twice with 100 microliters of PBS. 45 microliters of PBS containing 1% Triton X (product name, surfactant from Rohm & Haas) was then added to each well. The plate was vibrated for 1 minute to thoroughly destroy the cell membranes, and the absorbance at 475 nm was measured using a microplate reader, which was defined as the absorbance at time 0 minutes. Quickly after this, 5 microliters of 10 mM L-Dopa solution was added and the plate was transferred to an incubator kept at 37° C. to react for 60 minutes. The plate was vibrated for 1 minute and the absorbance (475 nm) at time 60 minutes was measured. The tyrosinase activity inhibition ratio (%) was defined as a decrease in the absorbance difference between time 0 minutes and time 60 minutes for the sample to which the plant extract was added compared with the absorbance difference between time 0 minutes and time 60 minutes for the sample to which the plant extract was not added. The results are shown in Table 1.

For a reference, the same testing was conducted on *Nepeta japonica* Maxim extract which was already known to inhibit tyrosinase activity. These results are also shown in Table 1. In the table, "−" indicates that no significant difference compared with the control was observed within a 5%-level of significance.

TABLE 1

| | Melanin production suppression effect | | | Tyrosinase activity suppression ratio (%) | |
|---|---|---|---|---|---|
| Concentration (wt %) | 0% | $10^{-3}$% | $10^{-2}$% | $10^{-3}$% | $10^{-2}$% |
| Musali extract | X | ◯ | | 76% | |
| Nepeta japonica Maxim. extract | X | X | X | — | 55% |

Table 1 indicates that the Musali extract has a superior melanin production suppression effect and tyrosinase activity suppression effect compared with the *Nepeta japonica* Maxim. extract.

5. Whitening Effect Testing

[Test Method]

66 testees were exposed to summer sunlight for 4 hours (2 hours a day for 2 days) and the skin of an inner lateral part of their upper arm was used as the subject of the test. Beginning after 5 days from the days they were exposed to the sunlight, each sample was applied to this skin once in the morning and once in the afternoon for 4 weeks. The panel was divided into 11 groups with 6 persons in each group.

Testing was conducted using lotion with the following formulas.

"Lotion"

| | wt % |
|---|---|
| (Alcohol phase) | |
| 95% ethanol | 25.0 |
| Polyoxyethylene (25-mole) hardened castor oil ether | 2.0 |
| Antioxidant/preservative | Appropriate amount |
| Perfume | Appropriate amount |
| Drug (specified in Table 2) | Amount specified in Table 2 |
| (Water Phase) | |
| Glycerine | 2.0 |
| Propylene glycol | 1.0 |
| Ion exchange water | Balance |

(Preparation Method)

The water phase and the alcohol phase were prepared separately and then solubilized.

[Evaluation Method]

The hypochromic effect after the application was evaluated based on the criteria below.

<Criteria>

⊚: Very effective or effective on 80% or more of the testees

○: Very effective or effective on 50% to less than 80% of the testees

Δ: Very effective or effective on 30% to less than 50% testees

×: Very effective or effective on less than 30% of the testees

Samples were prepared with the blend compositions described in the aforementioned test method, and the drugs listed in Table 2 were used to compare the whitening effect. The results are shown in Table 2.

TABLE 2

| Drug | Blend ratio (wt %) | Effect |
|---|---|---|
| Nothing added | 0 | X |
| Hydroquinone | 1.0 | Δ |
| Musali extract | 0.1 | Δ |
| Musali extract | 1.0 | ○ |
| Musali extract | 10.0 | ⊚ |

As clearly shown in Table 2, it was confirmed that the lotions with the Musali extract have a superior whitening effect.

For the purpose of assessing the tyrosinase activity suppression effect, the tyrosinase expression inhibition effect was tested by the following measurements (1) and (2).

(1) Measurement of Changes in the Tyrosinase Promoter Activity

A vector prepared by binding the tyrosinase promoter to the luciferase gene was introduced into B16 melanoma cultured cells derived from mice. After three hours, the Musali extract obtained as described above was added (0, 0.001, 0.002%). After 48 hours, the cells were lysed and the promoter activity was measured. The activity values were normalized by introducing the beta-galactosidase gene as the internal standard. The results are shown in FIG. 1. For comparison, changes in the activities of the SV40 promoter and the TFEC gene promoter are listed as well. The promoter activity with no added Musali extract was defined as 1. FIG. 1 indicates that the Musali extract suppresses the tyrosinase promoter activity.

Figure 2:
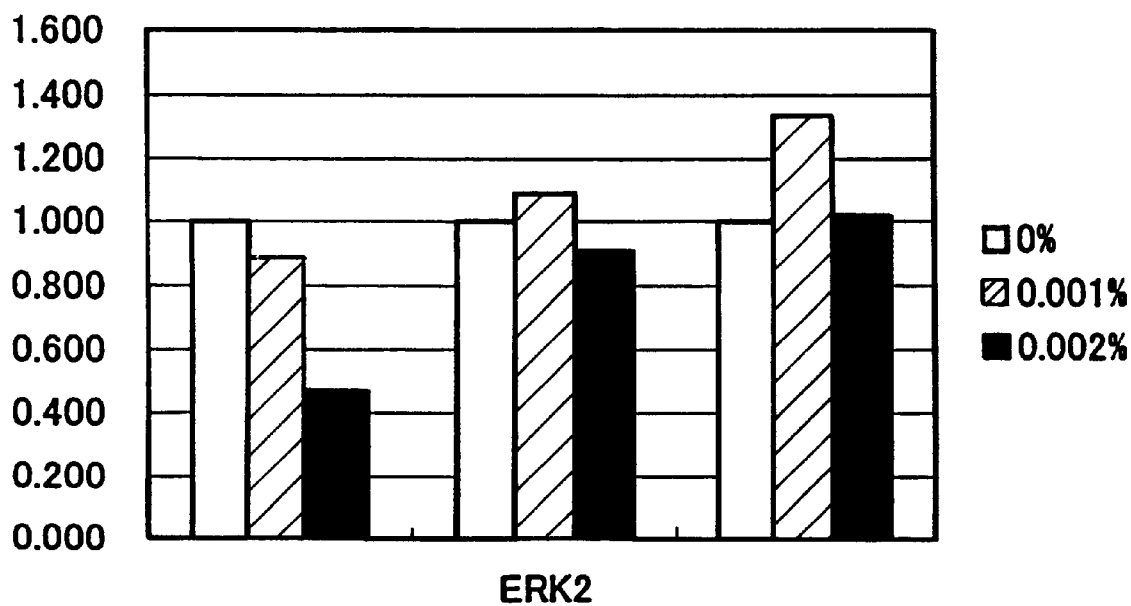
FIG. 2 is a graph showing changes in the degree of expression of the tyrosinase protein caused by the Musali extract.

(2) Measurement of Changes in the Degree of the Expression of the Tyrosinase Protein The Musali extract was added (0, 0.001, 0.002%) to B16 melanoma cultured cells derived from mice and, after 24 hours, the cells were lysed. With this, anti-tyrosinase antibodies were used in the Western blot method to detect the tyrosinase protein as a band, and the intensity was digitalized with a densitometer; the results are shown in FIG. 2. The protein level with no added Musali extract was defined as 1. FIG. 2 indicates that the Musali extract suppresses the degree of expression of the tyrosinase protein.

The results from the aforementioned (1) and (2) verify the effect of the Musali extract to suppress the degree of expression of tyrosinase on the promoter level Examples of the whitening endermic liniment of the present invention are shown in various formulations below. They are all highly stable and highly safe whitening endermic liniments with a superior whitening effect. The blend ratios are indicated in weight percent units.

Example 1

Burnishing Cream

| (Formula) | |
|---|---|
| Stearic acid | 6.0 |
| Sorbitan monostearic ester | 2.0 |
| Polyoxyethylene (20 mole) sorbitan monostearic ester | 1.5 |
| Arbutin | 7.0 |
| Sodium hydrogen sulfite | 0.03 |
| Propylene glycol | 10.0 |
| Musali extract | 0.0001 |
| Preservative/Antioxidant | Appropriate amount |
| Perfume | Appropriate amount |
| Ion exchange water | Balance |

(Preparation Method)

The Musali extract, arbutin, and propylene glycol were added to the ion exchange water and the mixture was heated to and kept at 70° C. (water phase).

Other ingredients were mixed, then heat-melted and the temperature was kept at 70° C. (oil phase). The oil phase was gradually added to the water phase, followed by pre-emulsification. Finally, the mixture was homogeneously emulsified by a homo-mixer and cooled to 30° C. while being thoroughly stirred.

Example 2

Whitening Neutral Cream

| (Formula) | |
|---|---|
| Stearyl alcohol | 7.0 |
| Stearic acid | 2.0 |
| Hydrated lanolin | 2.0 |
| 4-t-butyl-4'-t- | 3.5 |

-continued

| (Formula) | |
|---|---|
| methoxybenzoylmethane | |
| Squalane | 5.0 |
| 2-octyldodecyl alcohol | 6.0 |
| Polyoxyethylene (25-mole) cetyl alcohol ether | 3.0 |
| Glycerine monostearic ester | 2.0 |
| Placental extract | 0.1 |
| Propylene glycol | 5.0 |
| Musali extract | 10.0 |
| Perfume | Appropriate amount |
| Preservative/Antioxidant | Appropriate amount |
| Ion exchange water | Balance |

(Preparation Method)

The Musali extract, the placental extract, and propylene glycol were added to the ion exchange water and the mixture was heated to and kept at 70° C. (water phase). Other ingredients were mixed, then heat-melted and the temperature was kept at 70° C. (oil phase). The oil phase was added to the water phase, and after pre-emulsification, the mixture was homogeneously emulsified by a homo-mixer and cooled to 30° C. while being thoroughly stirred.

Example 3

Whitening Cold Cream

| (Formula) | |
|---|---|
| Solid paraffin | 5.0 |
| Beeswax | 10.0 |
| Petrolatum | 15.0 |
| Liquid petrolatum | 41.0 |
| Glycerine monostearic ester | 2.0 |
| Polyoxyethylene (20-mole) Sorbitan monolauric ester | 2.0 |
| Kojic acid | 2.0 |
| 4-t-butyl-4'-t-methoxybenzoylmethane | 3.5 |
| Soap powder | 0.1 |
| Borax | 0.2 |
| Musali extract | 0.1 |
| Ion exchange water | Balance |
| Perfume | Appropriate amount |
| Preservative/Antioxidant | Appropriate amount |

(Preparation Method)

The Musali extract, kojic acid, soap powder and borax were added to the ion exchange water, then heat-melted and kept at 70° C. (water phase). Other ingredients were mixed, then heat-melted and the temperature was kept at 70° C. (oil phase). The oil phase was gradually added to the water phase while stirring was conducted to allow the reaction to occur. When the reaction was complete, the mixture was homogeneously emulsified by a homo-mixer and then cooled to 30° C. while being thoroughly stirred.

Example 4

Whitening Emulsion

| | |
|---|---|
| Polyoxyethylene (20 mole) polyoxypropylene (2 mole) cetyl alcohol | 1.0 |

-continued

| | |
|---|---|
| Octyl-p-methoxycinnamate | 3.5 |
| Silicone KF96 (20 cs) (Shin-Etsu Chemical Co., Ltd.) | 20.0 |
| Liquid petrolatum (medium viscosity) | 3.0 |
| Propylene glycol | 5.0 |
| Arbutin | 2.0 |
| Sodium hydrogen sulfite | 0.03 |
| Glycerine | 2.0 |
| Ethanol | 15.0 |
| Carboxyvinyl polymer | 0.3 |
| Hydroxypropyl cellulose | 0.1 |
| KOH | Appropriate amount |
| Preservative | Appropriate amount |
| Musali extract | 20.0 |
| Ion exchange water | Balance |

(Preparation Method)

The hydrated alcohol extract of the Musali extract and arbutin were heat-dissolved in the ion exchange water and ethanol, and then propylene glycol and other water soluble ingredients were dissolved; the temperature was kept at 70° C. (water phase). Other oil-based ingredients were mixed, then heat-melted and the temperature was kept at 70° C. (oil phase). The oil phase was added to the water phase, and, after pre-emulsification, the mixture was homogeneously emulsified by a homo-mixer and then cooled to 30° C. while being thoroughly stirred.

Example 5

Whitening Emulsion

| | |
|---|---|
| Polyoxyethylene (20 mole) polyoxypropylene (2 mole) cetyl alcohol | 1.0 |
| Silicone KF96 (20 cs) (Shin-Etsu Chemical Co., Ltd.) | 2.0 |
| Liquid petrolatum (medium viscosity) | 3.0 |
| Propylene glycol | 5.0 |
| Ascorbyl glucoside | 5.0 |
| Octyl-p-methoxycinnamate | 3.5 |
| Glycerine | 2.0 |
| Ethanol | 15.0 |
| Carboxyvinyl polymer | 0.3 |
| Hydroxypropyl cellulose | 0.1 |
| KOH | Appropriate amount |
| Preservative | Appropriate amount |
| Musali extract | 7.0 |
| Ion exchange water | Balance |

(Preparation Method)

The Musali extract was heat-dissolved in the ion exchange water and ethanol, and then propylene glycol and other water soluble ingredients were dissolved; the temperature was kept at 70° C. (water phase). Other oil-based ingredients were mixed, then heat-melted and the temperature was kept at 70° C. (oil phase). The oil phase was added to the water phase, and, after pre-emulsification, the mixture was homogeneously emulsified by a homo-mixer and then cooled to 30° C. while being thoroughly stirred.

Example 6

Whitening Emulsion

| | |
|---|---|
| Polyoxyethylene (20 mole) polyoxypropylene (2 mole) cetyl alcohol | 1.0 |
| Silicone KF96 (20 cs) (Shin-Etsu Chemical Co., Ltd.) | 2.0 |
| Liquid petrolatum (medium viscosity) | 3.0 |
| Propylene glycol | 5.0 |
| Glycerine | 2.0 |
| 4-t-butyl-4'-t-methoxybenzoylmethane | 3.5 |
| Ethanol | 15.0 |
| Carboxyvinyl polymer | 0.3 |
| Hydroxypropyl cellulose | 0.1 |
| KOH | Appropriate amount |
| Preservative | Appropriate amount |
| Placental extract | 5.0 |
| Musali extract | 0.001 |
| Ion exchange water | Balance |

(Preparation Method)

The Musali extract and the placental extract were heat-dissolved in the ion exchange water and ethanol, and then propylene glycol and other water soluble ingredients were dissolved; the temperature was kept at 70° C. (water phase). Other oil-based ingredients were mixed, then heat-melted and the temperature was kept at 70° C. (oil phase). The oil phase was added to the water phase, and, after pre-emulsification, the mixture was homogeneously emulsified by a homo-mixer and then cooled to 30° C. while being thoroughly stirred.

Example 7

Whitening Emulsion

| | |
|---|---|
| Polyoxyethylene (20 mole) polyoxypropylene (2 mole) cetyl alcohol | 1.0 |
| Silicone KF96 (20 cs) (Shin-Etsu Chemical Co., Ltd.) | 2.0 |
| Liquid petrolatum (medium viscosity) | 3.0 |
| Propylene glycol | 5.0 |
| Glycerine | 2.0 |
| Ethanol | 15.0 |
| Carboxyvinyl polymer | 0.3 |
| Hydroxypropyl cellulose | 0.1 |
| KOH | Appropriate amount |
| Preservative | Appropriate amount |
| Kojic acid | 3.0 |
| Musali extract | 3.0 |
| Ion exchange water | Balance |

(Preparation Method)

The Musali extract and kojic acid were heat-dissolved in the ion exchange water, and then propylene glycol and other water soluble ingredients were dissolved; the temperature was kept at 70° C. (water phase). Other oil-based ingredients were mixed, then heat-melted and the temperature was kept at 70° C. (oil phase). The oil phase was added to the water phase, and, after pre-emulsification, the mixture was homogeneously emulsified by a homo-mixer and then cooled to 30° C. while being thoroughly stirred.

Example 8

Whitening Emulsion

| | |
|---|---|
| Stearic acid | 1.5 |
| Cetyl alcohol | 0.5 |
| Beeswax | 2.0 |
| Polyoxyethylene (20 mole) monooleic ester | 1.0 |
| Glyceryl monostearic ester | 1.0 |
| Ethanol | 10.0 |
| Arbutin | 20.0 |
| Sodium hydrogen sulfite | 0.03 |
| Propylene glycol | 5.0 |
| Musali extract | 0.5 |
| Ion exchanged water | Balance |
| Perfume | Appropriate amount |
| Preservative/Antioxidant | Appropriate amount |

(Preparation Method)

The Musali extract, arbutin, and propylene glycol were added to the ion exchange water and heat-dissolved, and the temperature was kept at 70° C. (water phase). The perfume was added to ethanol (alcohol phase). Other oil-based ingredients were mixed and heat-melted; the temperature was kept at 70° C. (oil phase). The oil phase was added to the water phase, and, after pre-emulsification, the mixture was homogeneously emulsified by a homo-mixer. The alcohol phase was added to this while being stirred. The mixture was then cooled to 30° C. while being thoroughly stirred.

Example 9

Emulsion

| (Formula) | |
|---|---|
| Microcrystalline wax | 1.0 |
| Beeswax | 2.0 |
| Lanolin | 2.0 |
| Liquid petrolatum | 20.0 |
| Squalane | 10.0 |
| Sorbitan sesquioleic ester | 4.0 |
| Polyoxyethylene (20 mole) sorbitan monooleic ester | 1.0 |
| Arbutin | 5.0 |
| Sodium hydrogen sulfite | 0.03 |
| Tranexamic acid | 5.0 |
| Propylene glycol | 7.0 |
| Musali extract | 0.1 |
| 4-t-butyl-4'-t-methoxybenzoylmethane | 3.5 |
| Ion exchange water | Balance |
| Perfume | Appropriate amount |
| Preservative/Antioxidant | Appropriate amount |

(Preparation Method)

The Musali extract, arbutin, tranexamic acid, and propylene glycol were added to the ion exchange water and the mixture was heated to and kept at 70° C. (water phase). Other ingredients were mixed, then heat-melted and the temperature was kept at 70° C. (oil phase). The oil phase was gradually added to the water phase while stirring was conducted, and the mixture was homogeneously emulsified by a homo-mixer and then cooled to 30° C. while being thoroughly stirred.

Example 10

Whitening Jelly (Formula)

| | |
|---|---|
| 95% ethyl alcohol | 10.0 |
| Dipropylene glycol | 15.0 |
| Polyoxyethylene (15 mole) oleyl alcohol ether | 2.0 |
| Arbutin | 0.5 |
| Sodium hydrogen sulfite | 0.03 |
| Ascorbyl distearate | 0.5 |
| Carboxyvinyl polymer (Product name: Carbomer 941) | 1.0 |
| Caustic potash | 0.15 |
| L-arginine | 0.1 |
| Musali extract | 2.0 |
| Perfume | Appropriate amount |
| Preservative | Appropriate amount |
| Ion exchange water | Balance |

(Preparation Method)

The Musali extract, arbutin, and Carbomer 941 were homogeneously dissolved in the ion exchange water. Dipropylene glycol, polyoxyethylene (15 mole) oleyl alcohol ether, and other ingredients were dissolved in 95% ethanol and this mixture was added to the water phase. The mixture was then neutralized and thickened with caustic potash and L-arginine.

Example 11

Peel-off Pack

| | |
|---|---|
| (Alcohol phase) | |
| 95% ethanol | 10.0 |
| Polyoxyethylene (15 mole) oleyl alcohol ether | 2.0 |
| 4-t-butyl-4'-t-methoxybenzoylmethane | 3.5 |
| Preservative | Appropriate amount |
| Perfume | Appropriate amount |
| (Water phase) | |
| Musali extract | 3.0 |
| Arbutin | 1.0 |
| Sodium hydrogen sulfite | 0.03 |
| Polyvinyl alcohol | 12.0 |
| Glycerine | 3.0 |
| Polyethylene glycol 1500 | 1.0 |
| Ion exchanged water | Balance |

(Preparation Method)

The water phase was prepared at 80° C. and cooled down to 50° C. The alcohol phase, prepared at room temperature, was then added to this, followed by homogeneous mixing and allowing to cool naturally.

Example 12

Whitening Pack with Powder

| | |
|---|---|
| (Alcohol phase) | |
| 95% ethanol | 2.0 |
| Preservative | Appropriate amount |
| Perfume | Appropriate amount |
| Coloring agent | Appropriate amount |
| Ascorbyl dioleate | 1.0 |
| (Water phase) | |
| Musali extract | 7.0 |
| Arbutin | 1.0 |
| Propylene glycol | 7.0 |
| Zinc flower | 25.0 |
| Kaolin | 20.0 |
| Ion exchanged water | Balance |

(Preparation Method)

The water phase was prepared at room temperature. The alcohol phase, prepared at room temperature, was then added to this, followed by homogeneous mixing.

Example 13

Whitening Water-absorbing Ointment

| | |
|---|---|
| Petrolatum | 40.0 |
| Stearyl alcohol | 18.0 |
| Japanese core wax | 20.0 |
| Polyoxyethylene (10 mole) monooleic ester | 0.25 |
| Glyceryl monostearic ester | 0.25 |
| Placental extract | 1.0 |
| Musali extract | 10.0 |
| Ion exchanged water | Balance |

(Preparation Method)

The Musali extract and the placenta extract were added to the ion exchange water and the temperature was kept at 70° C. (water phase). Other ingredients were mixed-dissolved at 70° C. (oil phase). The oil phase was added to the aforementioned water phase, and the mixture was homogeneously emulsified by a homo-mixer and cooled.

INDUSTRIAL APPLICABILITY OF THE INVENTION

The present invention can provide a whitening endermic liniment with a superior whitening effect which is highly stable and safe, as well as a method of whitening the skin. The whitening effect, melanin production suppression effect, and the tyrosinase activity suppression effect of the present invention were newly discovered in the present invention and are expected to have excellent application.

What is claimed is:

1. A skin whitening method comprising applying a whitening endermic liniment onto skin, said whitening endermic liniment comprising an extract from a plant of the Solanaceae family (Solanaceae), genus Withania (Withania), wherein application of said liniment upon skin causes suppression of tyrosinase activity and melanin production therein.

2. A skin whitening method comprising applying a whitening endermic liniment onto skin, said whitening endermic liniment comprising an extract from a plant of the Solanaceae family (Solanaceae), genus Withania (Withania), Musali (common name: Musali, scientific name: *Withania somnifera*).

* * * * *